United States Patent
Gerrans et al.

(10) Patent No.: US 10,661,061 B2
(45) Date of Patent: May 26, 2020

(54) CLEARANCE OF SINUS OSTIA BLOCKAGE

(71) Applicant: Sanovas Intellectual Property, LLC, Reno, NV (US)

(72) Inventors: Lawrence J. Gerrans, San Anselmo, CA (US); Erhan H. Gunday, Great Neck, NY (US)

(73) Assignee: Sanovas Intellectual Property, LLC, Reno, NV (US)

( * ) Notice: Subject to any disclaimer, the term of this patent is extended or adjusted under 35 U.S.C. 154(b) by 1387 days.

(21) Appl. No.: 14/479,822

(22) Filed: Sep. 8, 2014

(65) Prior Publication Data

US 2016/0067465 A1    Mar. 10, 2016

(51) Int. Cl.

| | |
|---|---|
| A61M 29/02 | (2006.01) |
| A61B 17/24 | (2006.01) |
| A61M 25/10 | (2013.01) |
| A61B 17/22 | (2006.01) |
| A61B 18/04 | (2006.01) |
| A61B 17/3207 | (2006.01) |
| A61B 18/02 | (2006.01) |

(52) U.S. Cl.
CPC .............. *A61M 29/02* (2013.01); *A61B 17/24* (2013.01); *A61B 17/22032* (2013.01); *A61B 17/320725* (2013.01); *A61B 18/0218* (2013.01); *A61B 2017/22061* (2013.01); *A61B 2017/22082* (2013.01); *A61B 2018/0212* (2013.01); *A61B 2018/046* (2013.01); *A61B 2218/002* (2013.01); *A61M 2025/105* (2013.01); *A61M 2025/1052* (2013.01); *A61M 2025/1086* (2013.01); *A61M 2210/0681* (2013.01)

(58) Field of Classification Search
CPC ............ A61B 17/24; A61B 17/320725; A61B 2017/246; A61B 2017/320741; A61B 18/04; A61B 17/32–2017/320098; A61B 17/320016–2017/32004; A61M 29/02; A61M 25/1011; A61M 25/104; A61M 2025/1015; A61M 2025/109; A61M 2025/1052; A61M 25/10–2025/1097; A61F 2/958

USPC ...................................... 606/20–31
See application file for complete search history.

(56) References Cited

U.S. PATENT DOCUMENTS 4,273,128 A * 6/1981 Lary ................ A61B 17/22031
                                                        604/913
4,630,609 A * 12/1986 Chin ................... A61M 25/104
                                                        604/101.01

(Continued)

OTHER PUBLICATIONS

U.S. Department of Health and Human Services, Centers for Disease Control and Prevention National Center for Health Statistics, Summary Health Statistics for U.S. Adults: National Health Interview Survey, 2009 (2010); 217 pages.

*Primary Examiner* — Tan-Uyen T Ho
*Assistant Examiner* — Charles M Wei
(74) *Attorney, Agent, or Firm* — Forge IP, PLLC

(57) ABSTRACT

A balloon catheter system and method for clearing blockage in the sinus ostium. The balloon catheter system and method employs a first balloon which dilates the sinus ostium while a second balloon removes an obstruction by resection. The system and method can then remove and/or drain any biological matter in the sinus. In some embodiments, the system employs an imaging device for viewing the anatomy and delivers irrigating and/or therapeutic agents to the sinus and/or sinus ostium.

15 Claims, 13 Drawing Sheets

(56) References Cited

U.S. PATENT DOCUMENTS

| | | | | |
|---|---|---|---|---|
| 4,832,688 A | * | 5/1989 | Sagae | A61B 17/0057 604/101.05 |
| 5,102,390 A | * | 4/1992 | Crittenden | A61M 25/104 604/103.1 |
| 5,181,920 A | * | 1/1993 | Mueller | A61B 17/3207 604/22 |
| 5,190,539 A | * | 3/1993 | Fletcher | A61B 18/00 606/25 |
| 5,281,200 A | * | 1/1994 | Corso, Jr. | A61M 25/104 604/102.02 |
| 5,338,301 A | * | 8/1994 | Diaz | A61M 25/09 600/434 |
| 5,372,601 A | * | 12/1994 | Lary | A61B 17/3207 606/159 |
| 5,415,636 A | * | 5/1995 | Forman | A61M 25/104 604/101.03 |
| 5,417,686 A | * | 5/1995 | Peterson | A61B 18/00 606/25 |
| 5,462,529 A | * | 10/1995 | Simpson | A61B 17/320758 604/101.04 |
| 5,514,092 A | * | 5/1996 | Forman | A61M 25/1011 604/101.03 |
| 5,571,086 A | * | 11/1996 | Kaplan | A61B 8/12 604/96.01 |
| 5,681,336 A | * | 10/1997 | Clement | A61B 17/320758 604/96.01 |
| 5,800,450 A | * | 9/1998 | Lary | A61B 17/3207 128/898 |
| 6,156,053 A | * | 12/2000 | Gandhi | A61M 25/1011 604/101.02 |
| 7,361,168 B2 | | 4/2008 | Makower et al. | |
| 7,727,226 B2 | | 6/2010 | Chang et al. | |
| 7,854,744 B2 | | 12/2010 | Becker | |
| 8,226,601 B2 | | 7/2012 | Gunday et al. | |
| 8,540,667 B2 | | 9/2013 | Gerrans et al. | |
| 8,597,239 B2 | | 12/2013 | Gerrans et al. | |
| 2002/0026145 A1 | * | 2/2002 | Bagaoisan | A61M 25/0009 604/96.01 |
| 2003/0105483 A1 | | 6/2003 | Hudson et al. | |
| 2003/0139802 A1 | * | 7/2003 | Wulfman | A61B 17/12022 623/1.15 |
| 2006/0004323 A1 | * | 1/2006 | Chang | A61B 17/24 604/28 |
| 2006/0063973 A1 | * | 3/2006 | Makower | A61B 1/00135 600/114 |
| 2006/0210605 A1 | * | 9/2006 | Chang | A61B 17/24 424/434 |
| 2007/0083158 A1 | * | 4/2007 | Hirszowicz | A61M 25/0119 604/96.01 |
| 2008/0132937 A1 | * | 6/2008 | Hartley | A61B 17/12045 606/194 |
| 2008/0154183 A1 | * | 6/2008 | Baker | A61M 1/0058 604/28 |
| 2010/0241155 A1 | * | 9/2010 | Chang | A61B 17/3421 606/196 |
| 2011/0082534 A1 | * | 4/2011 | Wallace | A61M 37/0092 623/1.11 |
| 2011/0282268 A1 | * | 11/2011 | Baker | A61B 17/24 604/20 |
| 2012/0071857 A1 | * | 3/2012 | Goldfarb | A61B 17/24 604/514 |
| 2012/0179158 A1 | * | 7/2012 | Stierman | A61B 18/1485 606/41 |
| 2012/0253266 A1 | * | 10/2012 | Qureshi | A61M 1/0084 604/28 |
| 2013/0116549 A1 | * | 5/2013 | Gunday | A61B 1/32 600/424 |

\* cited by examiner

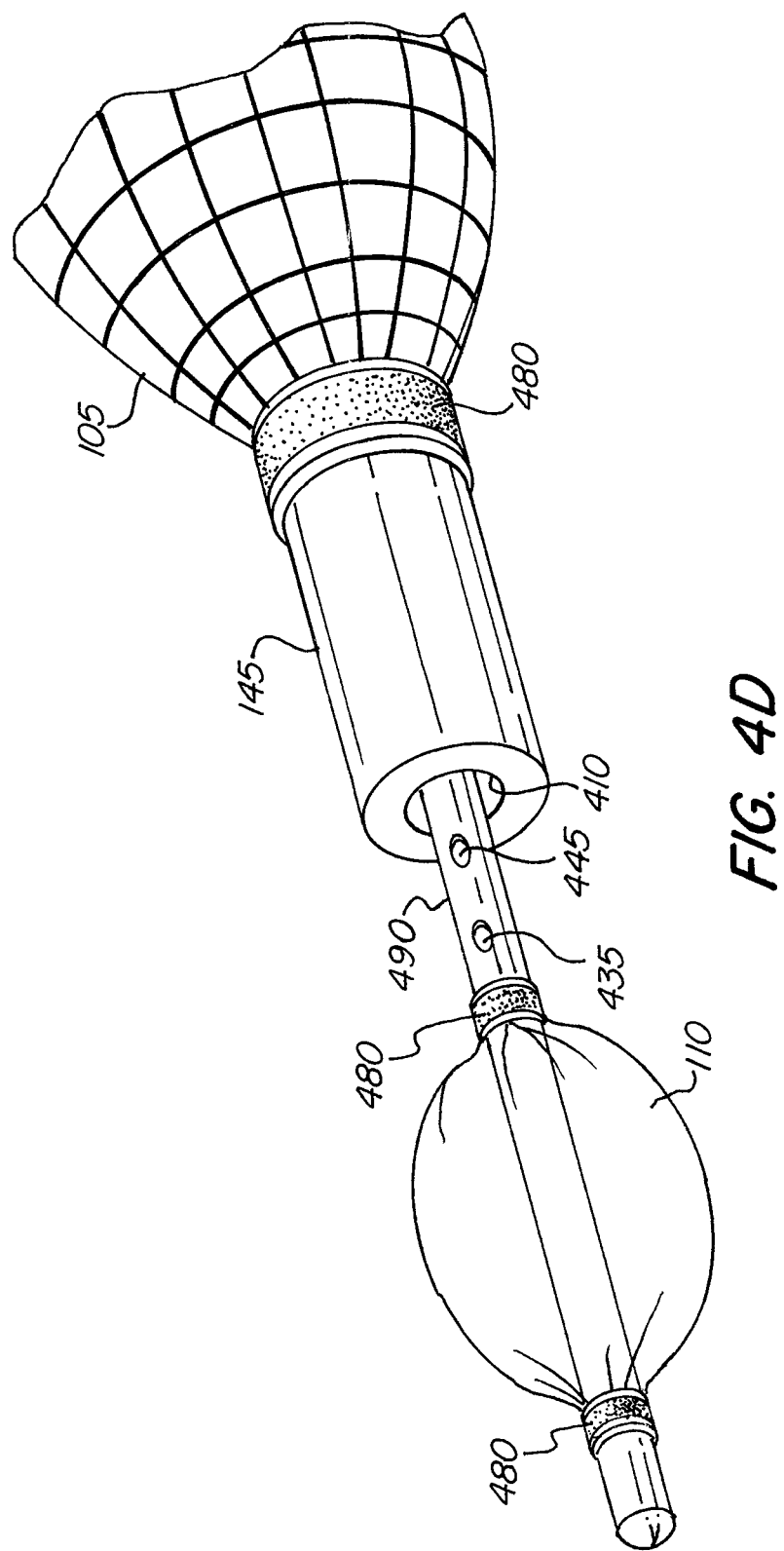

CLEARANCE OF SINUS OSTIA BLOCKAGE

FIELD OF THE INVENTION

The present invention relates to balloon catheters, and a method of using such catheters for treating conditions of the nose, nasal cavities and paranasal sinuses. More specifically, the present invention relates to a system and method of utilizing balloon catheters for dilating the sinus ostia, resecting biological material, and delivering therapeutic and/or diagnostic agents within the nose, nasal cavities and paranasal sinuses.

BACKGROUND OF THE INVENTION

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Recently, balloon catheters have been employed to release sinus congestion. Accordingly, various instruments and methods have been employed to perform these procedures.

The nasal cavity (or nasal fossa) is a large air filled space above and behind the nose in the middle of the face. The floor of the nasal cavity, which forms the roof of the mouth, is made up of the bones of the hard palate: the horizontal plate of the palatine bone posteriorly and the palatine process of the maxilla anteriorly. To the front of the nasal cavity is the nose, while the back blends, via the choanae, into the nasopharynx.

The paranasal sinuses are hollow cavities in the skull connected by small openings (ostia) to the nasal canal. Each ostium between a paranasal sinus and the nasal cavity is formed by bone covered by a layer of mucosal tissue. Normally, air passes into and out of the paranasal sinuses through the ostia and into the nasal canal.

The paranasal sinuses include the maxillary sinuses, the frontal sinuses, the ethmoid sinuses, and the sphenoid sinuses. The maxillary sinuses are also called the maxillary antra and are the largest of the paranasal sinuses. They are located under the eyes, in the maxillary bones. The frontal sinuses are superior to the eyes, in the frontal bone, which forms the hard part of the forehead. The ethmoid sinuses are formed from several discrete air cells within the ethmoid bone between the nose and the eyes. The sphenoid sinuses are in the sphenoid bone at the center of the skull base under the pituitary gland.

Sinusitis is an inflammation of the sinus lining commonly caused by bacterial, viral and/or microbial infections, as well as, structural issues such as ostial blockage. Symptoms include nasal congestion, facial discomfort, nasal discharge, headache, and fatigue. Sinusitis can be considered acute (lasting 4 weeks or less) or chronic (lasting 12 weeks or longer).

Sinusitis affects 29.3 million people each year, making it one of the most common health problems in the U.S. according to the U.S. Department of Health and Human Services, Centers for Disease Control and Prevention National Center for Health Statistics, Summary Health Statistics for U.S. Adults: National Health Interview Survey, 2009 (2010). It is responsible for large healthcare expenditures and a significant loss of workplace activity.

Another common ailment affecting the nose and paranasal sinuses is nasal polyps. Nasal polyps are benign masses that grow from the lining of the nose or paranasal sinuses. Nasal polyps often result from chronic allergic rhinitis or other chronic inflammation of the nasal mucosa. Nasal polyps are also common in children who suffer from cystic fibrosis. In cases where nasal polyps develop to a point where they can obstruct normal drainage from the paranasal sinuses, they can also cause sinusitis.

Various drugs have been used to treat sinusitis, including antibiotics and corticosteroid sprays. However, with the use of intranasal sprays, most of the spray does not actually enter the affected sinuses as there is commonly an obstruction blocking the drug from reaching the sinus. Accordingly, introduction of drugs directly into the sinuses has been proposed. For instance, U.S. Pat. No. 7,361,168 to Makower et al. discloses implantable devices that may be positioned within a naturally occurring or man-made cavity or passageway in a nostril, nasal cavity, sinus, etc. via balloon catheters.

Functional Endoscopic Sinus Surgery (FESS) is the most common surgical procedure for clearing blocked sinuses. However, the procedure involves removing bone and tissue, which can lead to post-operative pain, scarring and bleeding. The use of balloon catheters has been proposed in sinus surgery to minimize or eliminate many of these drawbacks.

One method of using balloon catheters involves creating a new opening from a sinus into the nose to dilate a sinus ostium or duct, or to excise a sinus. A further method involves inflating a balloon to break the bone surrounding the sinus in order to create a larger passage for fluid to drain. U.S. Pat. No. 7,854,744 to Becker discloses methods of performing balloon catheter astronomy of the maxillary ostium, middle meatal maxillary ostium, and inferior meatal ostium and a method of performing ethmoidectomy of the anterior ethmoid sinus, posterior ethmoid sinus, and sinusotomy of the frontal sinus. The methods generally involve pushing a balloon catheter through the ostia into the desired sinus cavity, inflating the balloon to 9 bars of pressure for 20 seconds, and then deflating the balloon. This may be repeated until the ostium is sufficiently enlarged. After final deflation, the catheter is removed from the enlarged ostium. The catheters employed by Becker utilize stainless steel catheters with radia of 0.13 inches, length of 4 to 10 inches, and wall thickness of at least 0.035 inches. The catheter tip contains a curved distal tip with an angle of 70° to 180°. The distal tip contains a balloon formed of polyethylene terephthalate with a length of 4 mm to 30 mm and working inflated diameter of 2 mm to 15 mm. The balloon has a distal neck and distal tapered region that is adhered to the distal tip of the catheter using an adhesive, such as cyanoacrylate.

In at least some procedures wherein it is desired to position a balloon catheter in the ostium of a paranasal sinus, it is necessary to advance the balloon catheter through complicated or tortuous anatomy in order to properly position the balloon catheter within the desired sinus ostium. There is also a degree of individual variation in the intranasal and paranasal anatomy of human beings, thus making it difficult to use the stiff-shaft pre-shaped balloon catheters of Becker for use in all individuals. The Becker patent describes the necessity of having a set of balloon catheters available, each having a particular fixed angle so that the physician can select the appropriate catheter for the patient's anatomy.

Accordingly, a series U.S. patents to Chang et al. (e.g. U.S. Pat. No. 7,727,226) disclose methods utilizing flexible balloon catheter devices for use in ear, nose and throat (ENT) procedures. Exemplary methods for improving drainage from a paranasal sinus that has a natural ostium comprise inserting a guidewire to a position near the ostium, using the guide to advance a balloon catheter within the ostium and using the balloon to dilate the natural ostium. A sizing balloon situated around the dilating balloon may be inflated using an imageable inflating medium, such as saline with radioopaque contrast agent or carbon dioxide gas. The distal region of the sizing balloon is imaged to enable the operator to estimate the size of the anatomical opening or the diameter of the narrowest region in a tubular anatomical region. Chang et al. also provide methods for treating mucocysts or other flowable substance containing structures located in the sinus by penetrating the structure, compressing the structure with, for example, the balloon of a balloon catheter, to force the contents out of the opening formed by the penetrator, advancing the penetrator into the sinus and opening in the cyst, and positioning the balloon in the sinus using the balloon to force the contents out of the opening formed by the penetrator.

Common risks with the above described methods and apparatuses, however, are the possibility of under or over-inflation of the balloon portion of the catheter. In the case of under-inflation, the effect of the catheterization on the ostium may be insufficient and therefore require additional treatments, adding to procedure times and increasing the risk of complications. In the case of over-inflation, the balloon catheter can fracture the ostium, leading to restenosis.

Imaging modalities, such as those used with a sizing balloon, cannot assess information regarding pressure or volume of inflated balloons. Variation in constriction responses associated with the nature of an obstruction highlight the importance of control over dilation set-points such as the rate of dilation, pressure, volume and the diameter of the inflated balloon. Many patient maladies are simply not remedied by these procedures because the methods are not efficient, safe, and reproducible, and/or the instruments employed lack the appropriate physiological measurement and/or feedback necessary to ensure the safety, efficacy, and reproducibility of the procedure.

Further, simple pressure control means, such as those described in US 2003/0105483 to Hudson et al., are not optimal because they only involve controlling pressure to a pre-set level through valve caps. The pre-set level can prevent extreme over-inflation, but requires the user to approximate a pre-set value and does not allow for real time monitoring and feedback as the balloon is within a nasal or paranasal lumen. The pre-set level also does not account for under-inflation when the diameter of an ostium is larger than anticipated.

Another common problem with prior art balloon catheter systems is only a single balloon is employed. A single balloon is inserted into the sinus in order to expand the sinus cavity. The balloon, however, cannot remove any blockages that may occur in the nasal passage or in the sinus while keeping the sinus cavity inflated, as the single balloon cannot inflate the sinus ostium, while also resecting any biological obstruction.

Hence, there is a significant need for systems and methods for deforming the sinus ostia that are capable of accurately and directly determining in vivo the size and optionally the compliance of areas of the nose, nasal cavities, and paranasal sinuses, such as the ostia. Additionally, there is a significant need for a second balloon attached to the catheter that is capable of resecting any blockage while the first balloon inflates the sinus cavity. Such systems and methods should be relatively simple to accommodate a single-use strategy.

SUMMARY OF THE INVENTION

Accordingly, it is an object of the present invention to provide methods for clearing sinus ostia without damaging the sinus ostia.

It is also an object of the present invention to remove biological matter from the paranasal sinuses using a balloon catheter without damaging the ostia.

It is a further object of the present invention to deliver diagnostic and/or therapeutic agents to the paranasal sinuses without damaging the ostia.

In order to overcome the deficiencies of the prior art and to achieve at least some of the objects and advantages listed, the invention comprises a method of clearing a paranasal sinus ostium of a patient. The method includes a method for clearing a sinus ostium of a patient, including inserting a catheter assembly into the sinus ostium, the catheter assembly having a resection balloon with a resecting surface and a dilation balloon, positioning the resection balloon at an obstruction in the sinus ostium, and the dilation balloon distal to the resection balloon, dilating a portion of the sinus ostium by inflating the dilation balloon, and resecting material from the obstruction by repeatedly inflating and deflating the resection balloon such that the resecting surface resects the material.

In some cases, the method further includes deflating the dilation balloon, and clearing resected material from the sinus ostium by removing the catheter assembly from the sinus ostium while the resection balloon is inflated.

In certain advantageous embodiments, the resecting surface comprises a mesh on an outer surface of the resection balloon, which in some cases, comprises elastane. In some embodiments, the mesh is impregnated with a therapeutic agent.

In some cases, the method further includes the step of delivering thermal energy to the mesh to aid the resection of the material. In certain embodiments the step of inflating the resection balloon comprises delivering a fluid that heats the resection balloon to aid the resection of the material, and in other embodiments, the step of inflating the resection balloon comprises delivering a fluid that cools the resection balloon to aid the resection of the material.

In some cases, the method further includes the step of flushing the sinus by delivering a fluid thereto, which in some cases, is saline.

In certain embodiments, the catheter assembly comprises a catheter having a radial outer wall, and the step of flushing the sinus comprises urging the fluid through a plurality of holes passing through the radial outer wall of the catheter.

In some cases, the method further includes the step of advancing a cannula over the catheter assembly into the sinus ostium and removing the catheter assembly from the sinus ostium to drain the sinus.

In certain cases, the method includes the step of delivering a therapeutic agent to the sinus. In some cases, the method includes the step of delivering a therapeutic agent to the obstruction.

In some cases, the method includes the step of viewing the sinus ostium and/or sinus by advancing an imaging device through the catheter assembly.

A system for clearing a sinus ostium of a patient is also provided, including a catheter assembly configured to be inserted into a sinus ostium, the catheter assembly comprising a resection balloon and a dilation balloon, wherein the dilation balloon is distal to the resection balloon such that, when the resection balloon is positioned at an obstruction in a sinus ostium and the dilation balloon is inflated, the dilation balloon dilates a portion of the sinus ostium, and wherein the resection balloon has a resecting surface that resects material from the obstruction in the sinus ostium when repeatedly inflated and deflated.

A system for clearing a sinus ostium of a patient is also provided that includes a catheter assembly comprising a resection balloon and a dilation balloon, the resection balloon having a resecting surface for resecting biological material, at least one fluid source that inflates the balloons by supplying fluid thereto, wherein the dilation balloon is located distal to the resection balloon such that, when the resection balloon is positioned at an obstruction in a sinus ostium and the dilation balloon is inflated, the dilation balloon dilates a portion of the sinus ostium, and wherein the fluid source repeatedly inflates and deflates the resection balloon by supplying fluid thereto such that the resecting surface resects biological material from the obstruction in the sinus ostium.

In certain advantageous embodiment, the resecting surface comprises a mesh on an outer surface of the resection balloon, which in some cases, comprises elastane. In certain cases, the mesh is impregnated with a therapeutic agent.

In certain advantageous embodiments, the system further includes an energy source that supplies thermal energy to the mesh to aid the resection of the material. In some embodiments, the fluid supplied to the resection balloon by the at least one fluid source is heated to aid the resection of the material, and in other embodiments, the fluid supplied to the resection balloon by the at least one fluid source is cooled to aid the resection of the material.

In certain advantageous embodiments, the catheter assembly comprises a catheter having a first lumen in fluid communication with the resection balloon, and a second lumen in fluid communication the dilation balloon. In some cases, the catheter assembly comprises a first catheter that includes the resection balloon, the first catheter having a first lumen in fluid communication with the at least one fluid source and the resection balloon through which fluid is communicated to the resection balloon, and a second catheter movably disposed in the first catheter, the second catheter including the dilation balloon and having a second lumen in fluid communication with the at least one fluid source and the dilation balloon through which fluid is communicated to the dilation balloon.

In certain advantageous embodiments, the system further includes an irrigation fluid source, wherein the catheter assembly comprises a catheter having a lumen in fluid communication with the irrigation fluid source, a distal end, and at least one opening at the distal end in communication with the lumen through which irrigation fluid is communicated to a sinus. In some embodiments, the system further includes a therapeutic agent source, wherein the catheter assembly comprises a catheter having a lumen in fluid communication with the therapeutic agent source, a distal end, and at least one opening at the distal end in communication with the lumen through which a therapeutic agent is communicated to a sinus.

In some embodiments, the catheter assembly comprises a catheter having a lumen for communicating fluid, a distal end, a radial outer wall, and a plurality holes passing through the radial outer wall at the distal end and in fluid communication with the lumen for communicating fluid to a sinus. In some cases, the catheter assembly includes a catheter and a cannula configured to slide over the catheter.

In certain advantageous embodiments, the catheter assembly comprises a catheter having an outer wall with a hole passing therethrough, the catheter having a lumen in fluid communication with the hole for communicating a therapeutic agent to the sinus ostium.

In some cases, the catheter assembly comprises a catheter having an outer wall with a hole passing therethrough, further comprising an imaging device movably disposed in the catheter and through the hole.

BRIEF DESCRIPTION OF THE DRAWINGS

FIG. 4D is an isometric view of the catheter system of FIGS. 1A-B using separate dilation balloon and resection balloon catheters.

FIGS. 5B-1 are exposed, side views of the balloon catheter system of FIG. 1 being used in the ostium and maxillary sinus of FIG. 5A.

DETAILED DESCRIPTION OF THE INVENTION

The exemplary embodiments of the present invention may be further understood with reference to the following description and the related appended drawings. The exemplary embodiments of the present invention are related to a device for dilating a paranasal sinus ostium, removing biological material, and delivering therapeutic and/or diagnostic agents to tissue in the nose, nasal cavity or paranasal sinuses of a patient. Specifically, the device uses two balloons to dilate the sinus ostium and resect any biological matter blocking the sinus cavity.

Figure 1A:
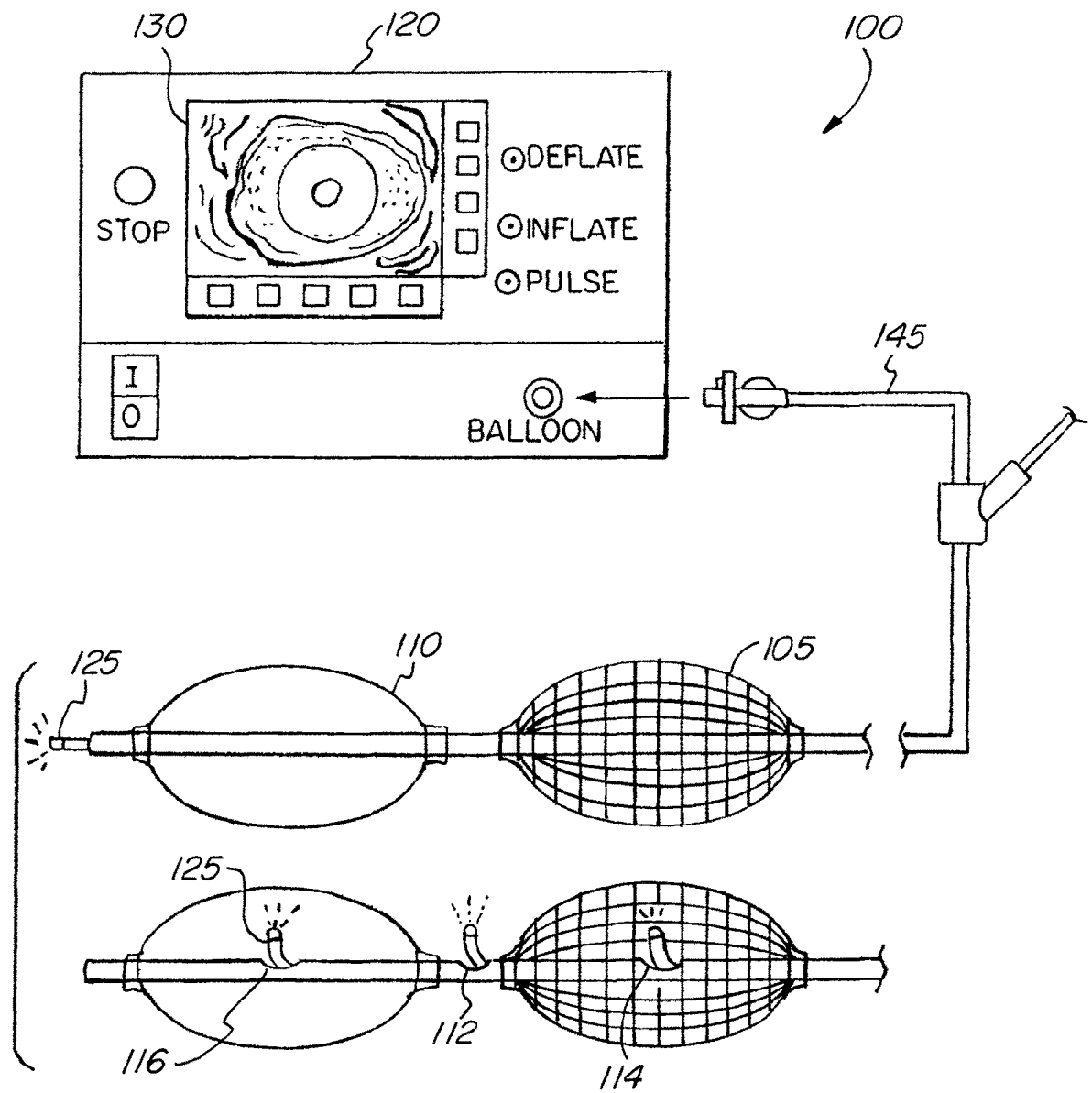
FIG. 1A is a schematic view of a balloon catheter system according to the present invention.
Figure 1B:
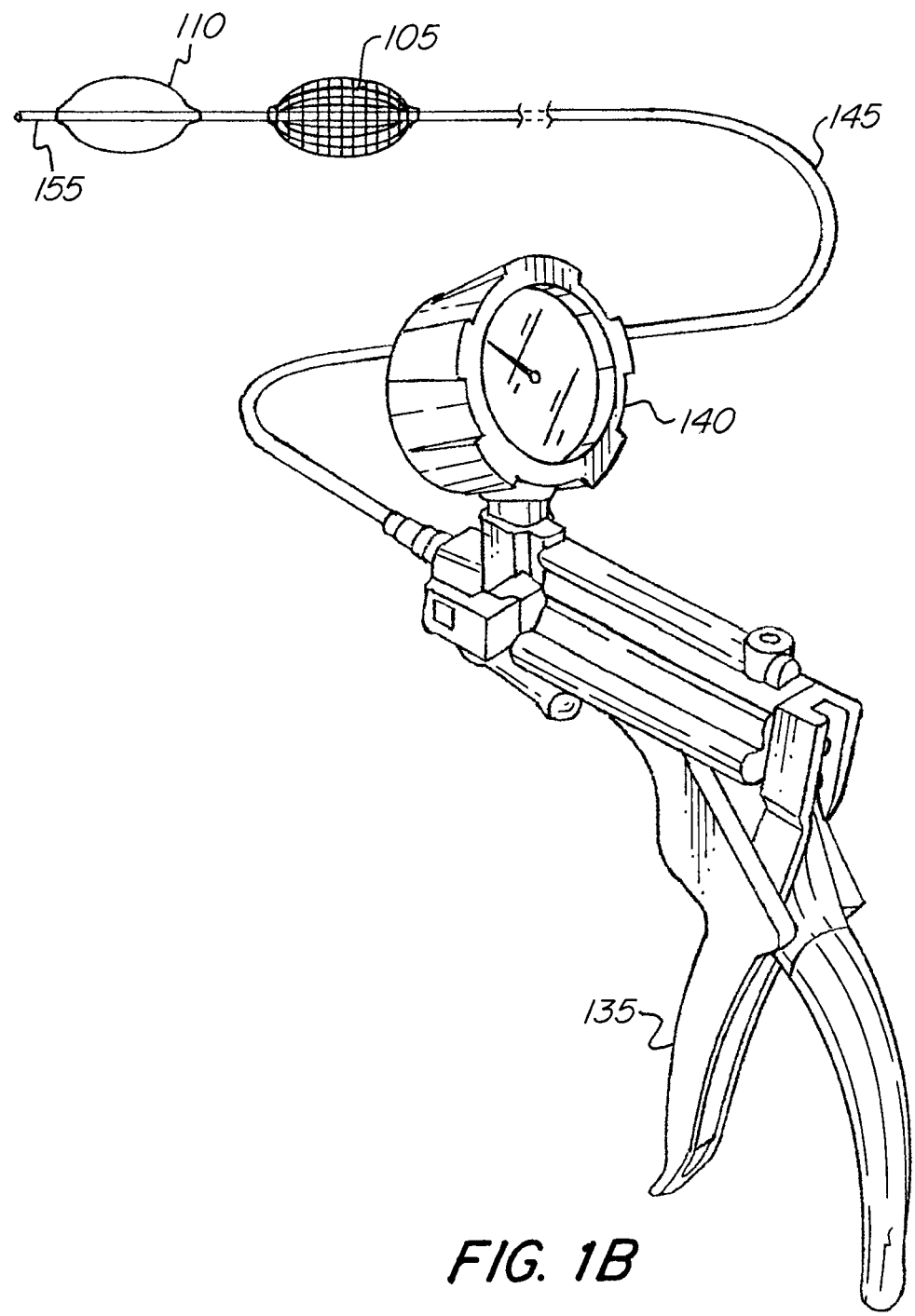
FIG. 1B is a perspective view of a balloon catheter system of FIG. 1A employing a hand pump.

As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention The basic components of one embodiment of the invention are illustrated in FIGS. 1A-B. A balloon catheter system (100) includes a fluid source (120) and a catheter (145). The catheter (145) includes a first balloon (105), and a second balloon (110) distal to the first balloon (105), in fluid communication with the fluid source (120). Fluid source (120) supplies a fluid, such as a gas, liquid, or mixture thereof, to inflate the balloons (105, 110). In some embodiments, the fluid is air. For some applications, an imaging device (125) is movably disposed in the catheter (145), and the catheter (145) has an outer wall with one or more openings (112, 114, 116) through which the imaging device (125) can be moved to view the anatomy from either inside or outside of the balloons (110, 115).

Any suitable fluid source may be used in accordance with the present invention. As shown in FIG. 1A, the fluid source may be an electro-pneumatic pump having controls on the front thereof, from which a physician or assistant can control the system (as well as a remote control unit). The pump (120) includes a display (130) to facilitate operation by the physician or to display multi-dimensional images of the anatomy in vivo. As shown in FIG. 1B, the fluid source (120) may also be a hand or foot actuated pump having an actuator (135) coupled to a gauge (140) for monitoring the flow of the fluid and/or pressure of the fluid delivered to balloons (115). The fluid may also be provided via a pneumo-mechanical or electro-mechanical pump.

Catheter (145) is made of a polyethylene or other suitable material and has an outer diameter of 1 mm to 20 mm, preferably 2 mm to 14 mm, most preferably 3 mm to 7 mm, and a length of about 15 to 40 centimeters. A bendable section (155) having a length of about 3 to 12 mm and typically capable of angulations of 5 to 45 degrees at the distal end of the catheter (145) serves as a safety tip. As a result, when the catheter (145) is inserted into a nasal cavity, it will bend instead of puncturing the walls of the cavity.

Balloons (105, 110) may be made of polyurethane, silicone, latex, Yulex, polyethylene, nylon or other suitable material, and are located near the distal end of the catheter (145) or at an otherwise desirable, predefined distance along the catheter (145). The balloons (105, 110) come in a variety of sizes and diameters, which can be selected to suit the particular application for which the device is being used. Typically, such balloons will have lengths of 5 mm to 50 mm, preferably 10 mm to 40 mm, and most preferably 15 to 40 mm. Such balloons will have diameters of 2 to 20 mm, preferably 3.5 mm to 15 mm, and most preferably, 5 to 7 mm. Balloons (105, 110) may be either compliant, non-compliant, or one balloon may be compliant while the other balloon is non-compliant.

The pump (120) supplies the air at a pressure of approximately 2 atmospheres in order to be able to inflate such balloons to full size, with the particular value depending on the particular balloon and particular location. By employing relatively low pressures that approximate physiologic conditions, the methods of the present invention have a minimum impact on the physical structure of the nasal cavities. In particular, the structure of any polyp or mucous congestion along the walls of the ostium can be assessed without significant mechanical disruption (as would be the case with methods that determine wall compliance during high pressure).

The first balloon (105) comprises a resection balloon, which includes a resecting surface for resecting undesired biological material in a sinus ostium. For example, the resecting surface may comprise a fiber mesh located on the outer surface of balloon (105). It should be noted, however, that various textures may be employed for the resecting surface of balloon (105). The second balloon (110) comprises a dilation balloon, which dilates a portion of the sinus ostium when inflated.

Figure 2A:
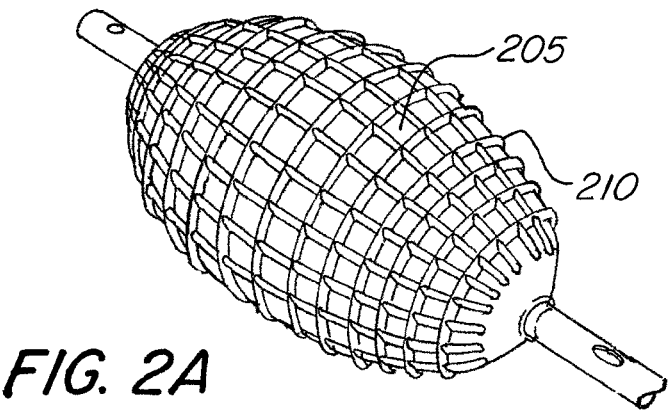
FIGS. 2A-C are perspective views of a resection balloon employed in the balloon catheter system of FIGS. 1A-B.
Figure 2B:
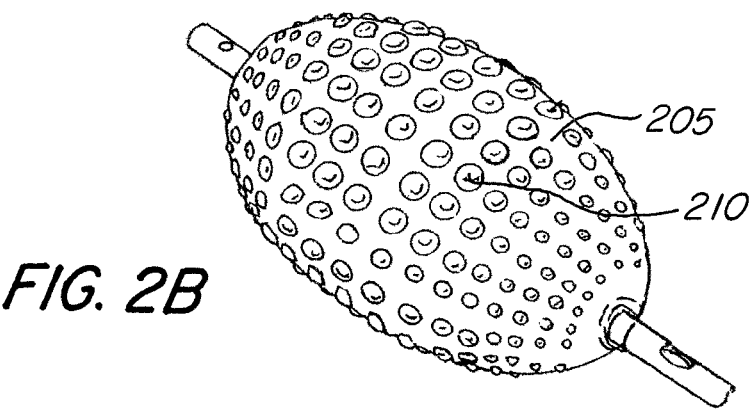
Figure 2C:
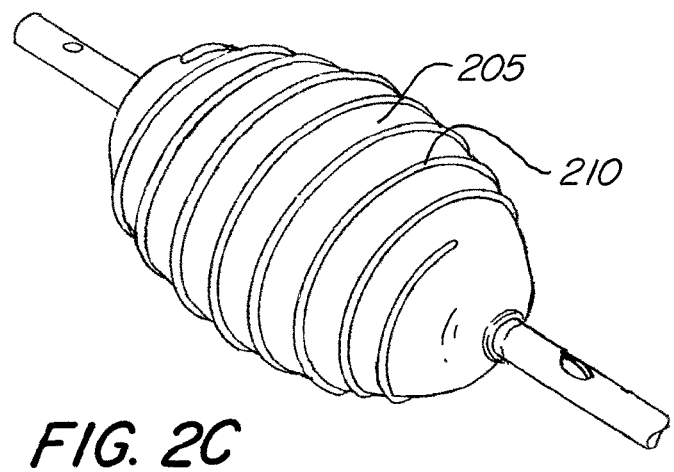

As best seen in FIGS. 2A-C, in order to produce a resection surface for resection balloon (105), the surface (205) of the resection balloon (105) has a plurality of protrusions (210). As noted above, these could be formed by a fiber mesh affixed to the surface (205) of balloon (105) during or after the molding process. The fiber mesh may be made of elastane, cotton, lycra, polyurethane, composite springs, or other appropriate material. Alternatively, dimensional surface structures or inflatable sinuses that are encapsulated in the surface substrate (205) of resection balloon (105) may be used to produce the surface protrusions (205).

The protrusions (210), forming the resecting surface of balloon (105) can have various shapes and configurations, depending on a particular application. For example, as shown in FIG. 2A, the outer surface (205) of balloon (105) has outwardly extending protrusions (210) that form a lattice-like structure on the surface of balloon (105). In another advantageous embodiment shown in FIG. 2B, the protrusions (210) are in the form of dimples that extend outwardly from the outer surface (205) of balloon (105). In yet another advantageous embodiment illustrated in FIG. 2C, the protrusions (210) form a spiral-like pattern that extends circumferentially on the outer surface (205) of balloon (105). It should be noted that any other shapes and configurations of the surface protrusions can be used in accordance with the present invention.

Additionally, resection balloon (105) may be used to abrade bodily tissue to perpetuate fluid extravasation processes and stimulate associated cellular absorption of diagnostic and/or therapeutic agents into the adjacent tissues as detailed in U.S. Pat. Nos. 8,540,667 and 8,597,239 to Gerrans et al., the specifications of which are hereby incorporated by reference herein in their entirety. Moreover, the textured outer surface of the balloon (105) can also act as a gripping surface for attachment to bodily tissues in order to prevent slippage during other aspects of the procedure, such as, for example, when the second balloon (110) is positioned or inflated, or as another example, when irrigation fluid is delivered to the sinus, as is further described below.

In certain advantageous embodiments, the mesh (210) located on the balloon (105) is impregnated with a therapeutic agent in order to facilitate removal of the unwanted biological material and treat the surrounding tissue. Alternatively, the resection balloon (105) may also have a sponge-like or other type of material on its outer surface for delivering a drug directly to the target site, which may even be retained on the balloon via the mesh (210).

Figure 3:
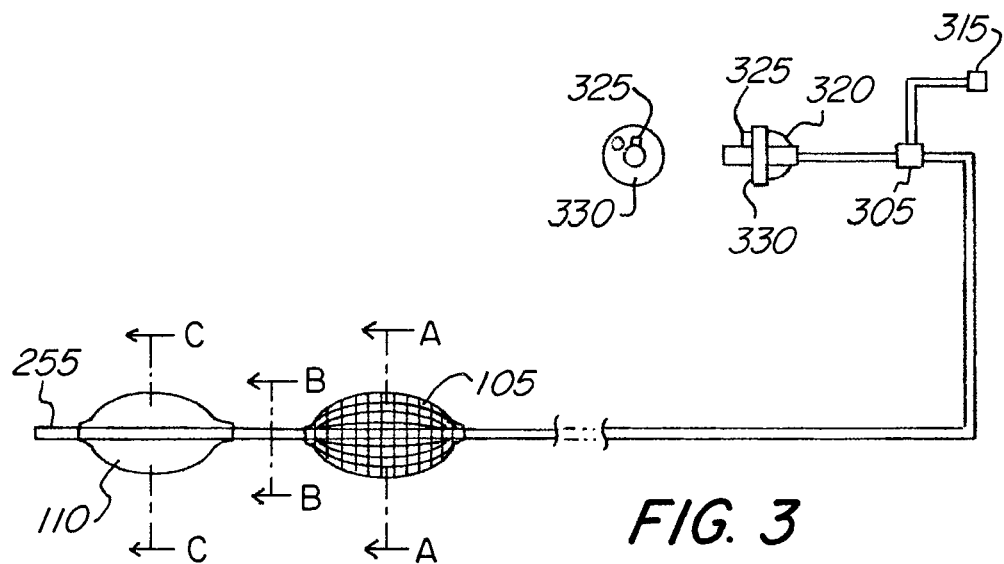
FIG. 3 is a schematic view of the balloon catheter of FIGS. 1A-B.

As shown more clearly in FIGS. 3-4, the catheter (145) includes at least one inner lumen breakout Y junction (305) to facilitate the introduction of a guide wire, additional catheter, air bypass, drug delivery, or visualization conduit. The proximal end of the inner lumen (405) after Y junction (305) is terminated with a luer connector (315). The outer lumens (420, 430, 440, 450) are terminated at their proximal end with a keyed connector (320), which includes a key (325) and a balloon identification plate (330).

The Y junction (305) serves several purposes. First, it brings out a separate, inner lumen (405) of the catheter (145) to a suitable connector, such as the aforementioned luer connector (315), in order to provide an independent passage. Additionally, the Y junction (305) also includes a shut-off valve (not shown) for stopping balloons (105, 110) from deflating. This may be used, for example, when it is required to leave the inflated balloon in place for a lengthy period of time.

Catheter (145) is terminated at the proximal end with the keyed balloon identification plate (330). Balloon identification plate (330) is used to electronically detect the catheter (145) when it is inserted into the pump (120) and to identify the particular type of balloon catheter being used. The key (325) orients the connector (320) and the identification plate (330) in such a way that the balloon type can be identified by the pump (120) using electro-optical or electro-mechanical means.

Each type of balloon that can be used with the pump (120) is characterized, and the balloon profile data is registered in lookup tables. By identifying the type of balloons (105, 110) that are connected to the pump (120), the appropriate profile data can be retrieved and used to ensure that the appropriate pressure, volume, flow, and timing adjustments can be made to safely and effectively operate the balloons (105, 110). The balloon profile data contained in the lookup table, along with appropriate pressure and flow measurements (as further discussed below), allows one to make biological material density approximations. This balloon profile data, along with approximated bodily lumen (ostium or sinus) diameter, biological material density, as well as any user commands, is used to adjust the amount of gas the pump (120) delivers to the balloons (105, 110) in order to achieve the desired inflation and deflation amounts.

Figure 4A:
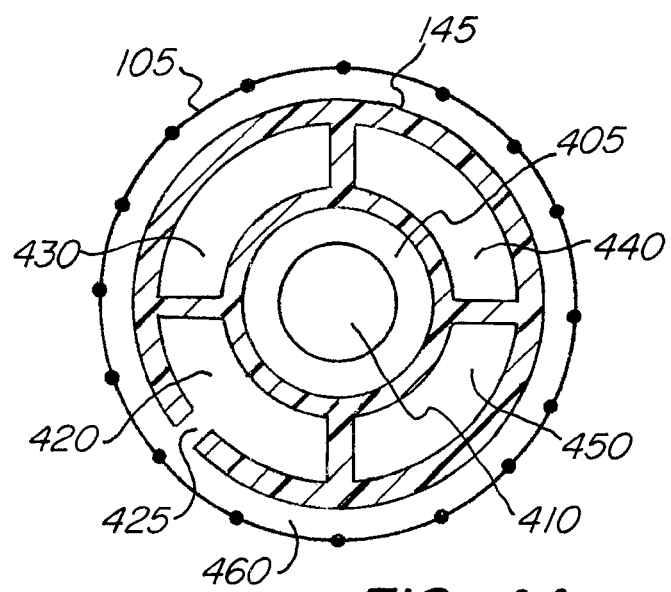
FIG. 4A is a cross sectional view of the catheter of FIG. 3 along line A-A.
Figure 4B:
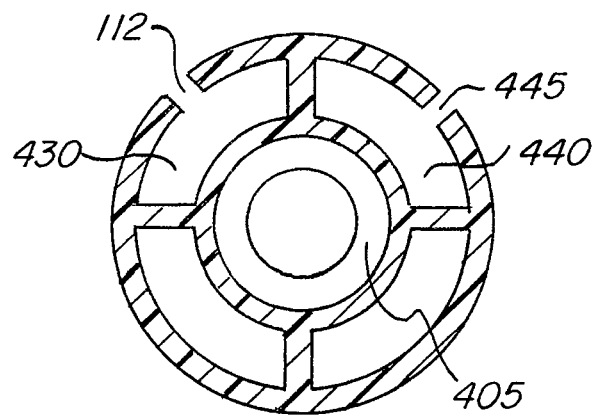
FIG. 4B is a cross sectional view of the catheter of FIG. 3 along line B-B.
Figure 4C:
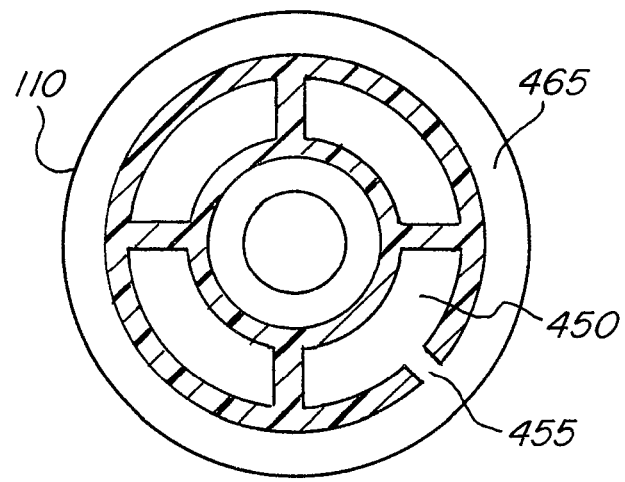
FIG. 4C is a cross sectional view of the catheter of FIG. 3 along line C-C.

Referring to FIGS. 4A-C, partial cross-sectional views of the balloons (105, 110) and catheter (145) in one embodiment of the invention are shown. In this embodiment, catheter (145) includes an inner lumen (405) and four outer lumens (420, 430, 440, 450). It should be noted, however, that these lumens may be provided in different physical arrangements, and further, that more or less lumens may be provided, depending on what fluids and/or devices need be delivered to the sinus ostia.

Referring first to FIG. 4A, a cross-sectional view at the location of resection balloon (105) is shown. Catheter (145) has an inner lumen (405) that is used as a conduit for a guide wire (410) for accurately positioning the catheter (145) when inserting the catheter (145) into the sinus ostium. Outer lumens (420, 430, 440, 450) extend through catheter (145), but only lumen (420) has openings at this location. Specifically, one or more openings (425) pass through the wall of catheter (145) and into the inner chamber (460) of resection balloon (105). As a result, fluid source (120) supplies fluid through lumen (420) and openings (425) to inflate resection balloon (105).

Referring next to FIG. 4B, a cross-sectional view at the location of catheter (145) between balloons (105, 110), is shown. At this location, only lumens (430, 440) have openings.

Specifically, an opening (112) passes from lumen (430) and through the wall of catheter (145) into the sinus ostium. Imaging device (125) can be movably disposed in lumen (430) and advanced through the opening (112) in order to view surrounding tissue during the insertion or operation of the balloons in the bodily cavity. Alternatively or in addition to opening (112), the catheter (145) may be provided with openings (114) and/or (116), such that that imaging device (125) can be moved inside balloons (105, 110) in order to view the anatomy through one or both balloons, as depicted in FIG. 1A. It should be noted that the system (100) may also provide for the advancement of an imaging device (125) through the end of catheter (145), for example, through inner lumen (405), in order to view the sinus, as is also shown in FIG. 1A. Such an arrangement allows the tissue in front of the catheter to be viewed by imaging device (125) during the insertion of the balloon catheter system (100) into a bodily cavity.

Returning again to FIG. 4B, catheter (145) also includes one or more openings (445) that pass from lumen (440), through the wall of catheter (145) and into the sinus ostium for supplying a therapeutic and/or diagnostic agent thereto. It should be noted, however, that in some embodiments, openings (445) may instead be positioned along the catheter (145) at a location inside of a balloon (105, 110), and the wall of the balloon (105, 110) has at least one opening therethrough, such that the therapeutic and/or diagnostic agent is delivered into the balloon (105, 110) via lumen (440) and then to the biological material through the openings in the wall of the balloon.

In this way, the lumen (440) is used to deliver a therapeutic and/or diagnostic agent to the sinus ostium, such as, for example, a medicinal drug. Likewise, lumen (440), or an additional lumen, may open at the end of catheter (145), such that an agent can be delivered to the sinus, as is described further below. Lumen (440) can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, stents and scaffolds, and warm or cold saline to flush the paranasal sinus ostium.

Examples of diagnostic or therapeutic agents are contrast agents, a pharmaceutically acceptable salt or dosage form of an antimicrobial agent (e.g., antibiotic, antiviral, anti-parasitic, antifungal, etc.), an anesthetic agent, an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, or immunomodulator), an allergen or another substance that causes secretion of mucous by tissues, anti-proliferative agents, hemostatic agents to stop bleeding, cytotoxic agents (e.g. alcohol), biological agents such as protein molecules, stem cells, genes or gene therapy preparations, etc.

Antimicrobial agents can include, but are not limited to, acyclovir, amantadine, amikacin, gentamicin, tobramycin, amoxicillin, amphotericin B, ampicillin, sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clavulanate, clotrimazole, ciprofloxacin, clarithromycin, clindamycin, dapsone, dicloxacillin, doxycycline, erythromycin, fluconazole, foscarnet, ganciclovir, atifloxacin, imipenem, cilastatin, isoniazid, itraconazole, ketoconazole, metronidazole, nafcillin, nystatin, penicillin, penicillin G, pentamidine, piperacillin, rifampin, quinupristin-dalfopristin, ticarcillin, trimethoprim, sulfamethoxazole, tazobactam, valacyclovir, vancomycin, mafenide, silver sulfadiazine, mupirocin, nystatin, triamcinolone, butoconazole, miconazole, tioconazole, and combinations thereof.

Anti-inflammatory agents can include, but are not limited to, beclomethasone, flunisolide, fluticasone proprionate, triamcinolone acetonide, budesonide, loterednol etabonate, mometasone, aclometasone, desonide, hydrocortisone, betamethasone, clocortolone, desoximetasone, fluocinolone, flurandrenolide, prednicarbate, amcinonide, desoximetasone, diflorasone, fluocinolone, fluocinonide, halcinonide, clobetasol, salicylic acid derivatives, aspirin, sodium salicylate, choline magnesium trisalicylate, salsalate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, piroxicam, meloxicam, nabumetone, rofecoxib, celecoxib, etodolac, nimesulide and combinations thereof.

Exemplary decongestants include, but are not limited to, pseudoephedrine, xylometazoline, oxymetazoline, phenylephrine, epinephrine, and combinations thereof.

Mucolytic agents can include, but are not limited to, acetylcysteine, guaifenesin and combinations thereof.

Anti-histamines can include, but are not limited to, cromolyn, nedocromil, azelastine, diphenhydramine, loratidine, and combinations thereof.

An exemplary anti-cholinergic is ipratropium bromide.

Diuretics can include, but are not limited to, furosemide and/or hyperosmolar agents such as sodium chloride gel or other salt preparations.

In certain applications, it may be desirable to locally deliver, in a similar manner, agents that will facilitate photodynamic therapy. Likewise, various forms of energy can be delivered locally, including laser, microwave, RF, cryogenic, and thermal energies. Such delivery can be accomplished, for example, by simply advancing an appropriate probe through one of the aforementioned lumens and corresponding opening.

Referring next to FIG. 4C, a cross-sectional view at the location of dilation balloon (110) is shown. Only lumen (450) has openings at this location. Specifically, one or more openings (455) pass through the wall of catheter (145) and into the inner chamber (465) of dilation balloon (110). As a result, fluid source (120) supplies fluid through lumen (450) and openings (455) to inflate dilation balloon (110).

In the above-described embodiment, a single catheter (145) is used to deflate both first balloon (105) and second balloon (110). However, it should be noted that, in other embodiments, the second balloon (110) is part of a second catheter (490), as shown in FIG. 4D. In such cases, catheter (445) may be movably disposed through, for example, inner lumen (405) of catheter (145), and the inflation lumens for first balloon (105) and second balloon (110) are therefore in separate catheters.

The balloons (105, 110) may include imaging markers, such as radio opaque rings (480), located at or near the ends thereof. Such markers can be selected and appropriately positioned in order to reflect the relevant waves of various imaging modalities in order to allow the use of such modalities to assist with the precise positioning of the balloons (105, 110).

Figure 5A:
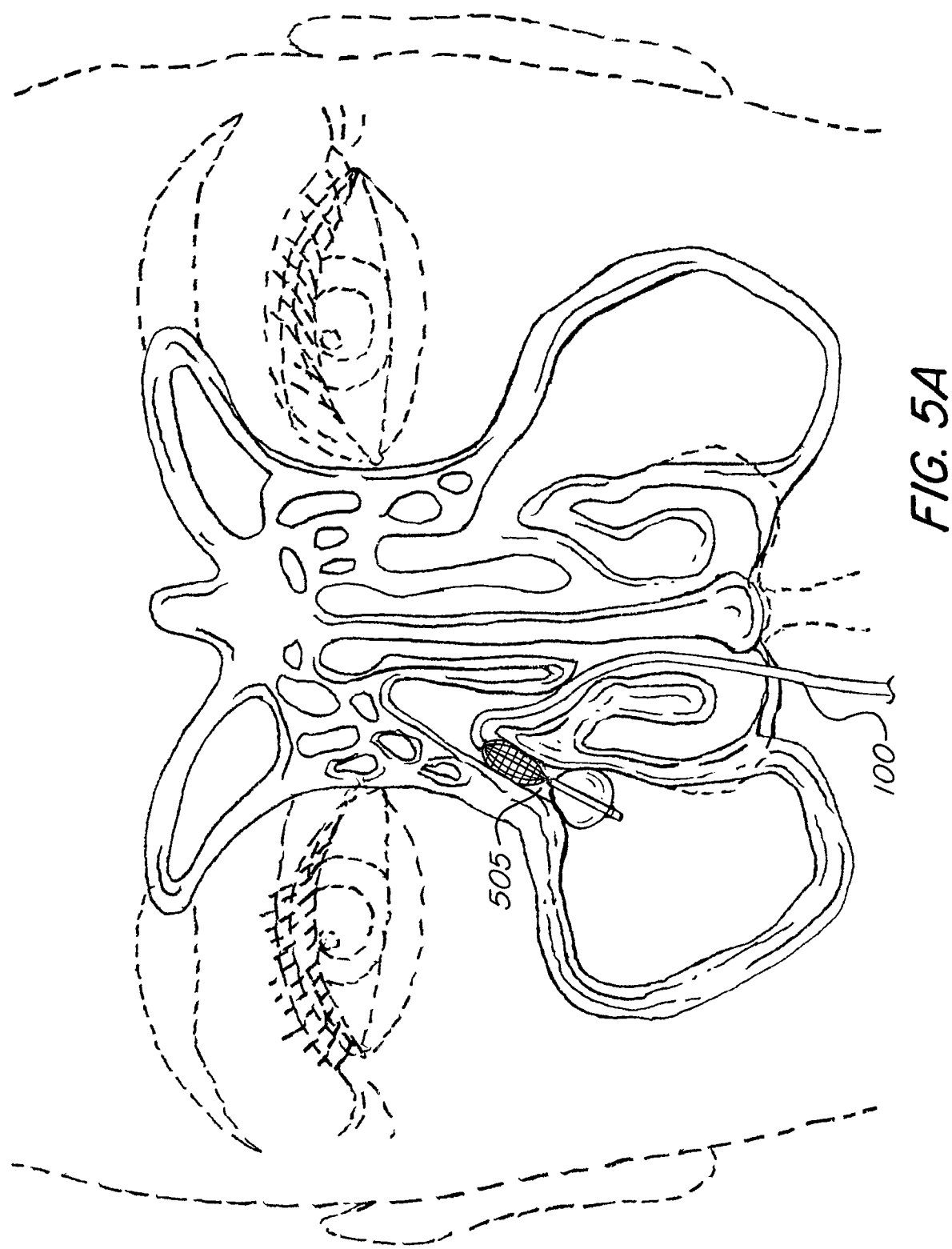
FIG. 5A is a partially exposed, front view of a method of using the catheter of FIG. 1 in a sinus ostium.

The use of the catheter system (100) for accessing and resecting an obstruction in a maxillary sinus ostium (505) is generally depicted in FIG. 5A. One method of employing a catheter system (100) in accordance with the invention is illustrated stepwise in FIGS. 5B-I.

Figure 5B:
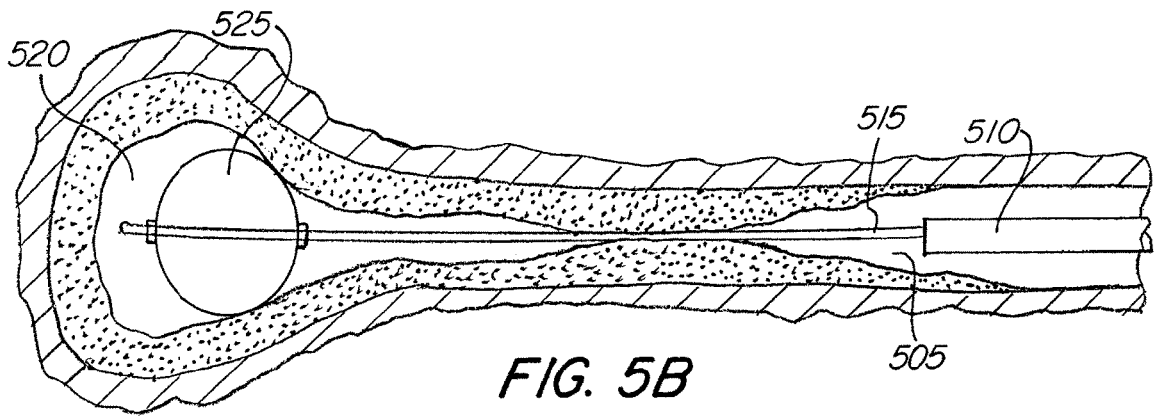

Referring to FIG. 5B, a guide catheter (510) is first introduced through a nostril and advanced in the paranasal anatomy. The guide catheter (510) is flexible and steerable or pre-shaped such that a proximal bent, curved, or angled region allows guide catheter (510) to be positioned around the inferior turbinate and the middle turbinate. A guidewire (515) or a suitable diagnostic or therapeutic device may then be introduced through the lumen of guide catheter (510) into the maxillary sinus (520). The guidewire (515) may include a balloon (525) which is inflated once in the maxillary sinus to anchor the guidewire in place. If guide catheter (510) was used, it may then be withdrawn.

Figure 5C:
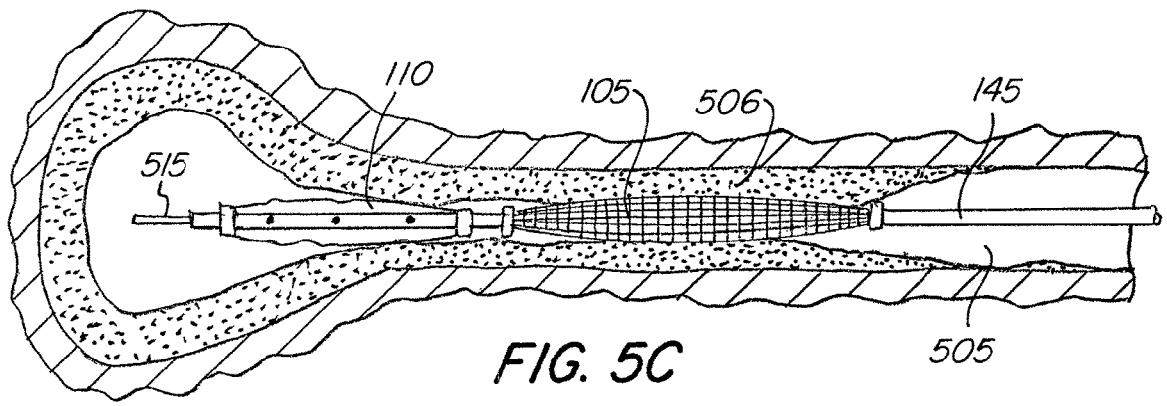

If desired, a visual inspection via an endoscope, CT-scan, x-ray, or other anatomical mapping means may be conducted. Referring to FIG. 5C, a balloon catheter system (100) is then selected, and the deflated device is inserted into a nasal passage until resection balloon (105) is in the desired portion of the sinus ostium (505). Dilation balloon (110) is positioned distal to resection balloon (105) when the resection balloon (105) is positioned at an obstructed portion (506) of the sinus ostium (505), and may be positioned partially in the sinus (520) and partially in the sinus ostium (505). If a guidewire (515) is used, the positioning of resection balloon (105) and dilation balloon (110) may be accomplished by inserting the proximal end of guidewire (515) into inner lumen (405) of catheter (145) and sliding catheter (145) over guide wire (515). If the guidewire (515) includes an anchoring balloon (525), this balloon is then deflated, and the guidewire (515) is pulled out through the inner lumen (405) of catheter (145), either before or after the inflation of the dilation balloon (110) described below. Catheter (145) is connected to pump (120) (further described in detail below), at which time pump (120) determines the type of balloon catheter that has been inserted. Pump (120) may render a multi-dimensional image of the anatomy in vivo on the display based on the balloon profile data alone or in concert with direct and/or indirect imaging methods and imaging guidance.

Figure 5D:
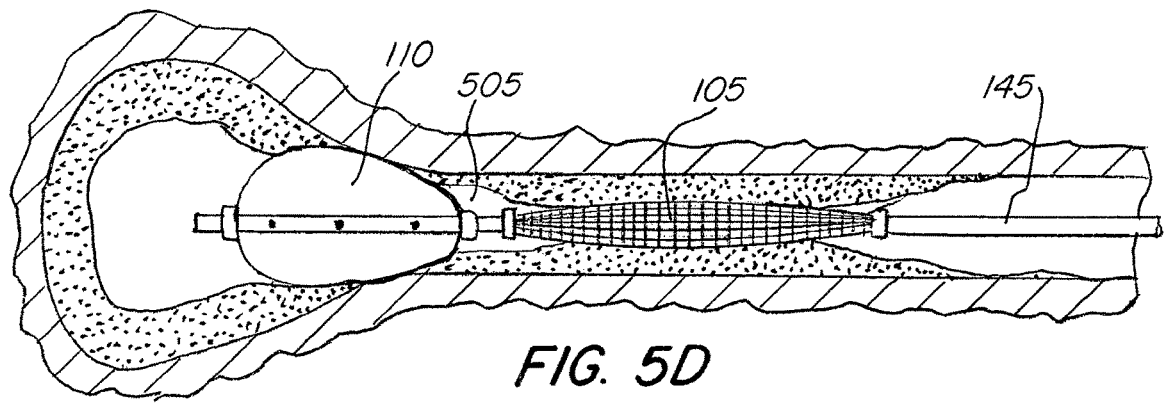

Referring to FIG. 5D, dilation balloon (110) is inflated by pump (120). This dilates the sinus ostium (505), which provides resection balloon (105) with some room to inflate and deflate. Pump (120) (which knows the type of balloon to which it is connected) supplies fluid at an air pressure of approximately 2 atmospheres for a fixed amount of time, and the flow is measured (after the physician presses an inflate button on the pump). Each "inflate" command will inflate the balloon by an incremental amount based on the type of balloon that is connected. This incremental inflation is accomplished by opening an inflate valve for a set amount of time while a deflate valve remains closed. In this way, the balloon is inflated to the size desired by the user. Alternatively, pressing and holding the inflate button will inflate the balloon in a continuous fashion.

While inflating, the flow of gas (ml/sec) is measured. After closing the inflate valve, the balloon pressure is measured, and an approximation of the volume V is made based on the ideal gas law (V=nRT/P) and a lookup table, which contains balloon characteristics and universal constants. Here, T is assumed constant at 310° K (body temperature can be measured and entered into the equation as well), R is a gas law constant, n is moles of gas, which is proportional to the measured flow, and P is the measured pressure. With each incremental inflation, V is recalculated, and the relative volume change (V2−V1) is displayed. Knowing the shape of the balloon from the balloon identification, and using the data from the lookup table, the relative change in balloon diameter (D2−D1) is also calculated and displayed. On the basis of information obtained during this step, the balloon catheter (145) may be repositioned, and this process repeated, if necessary.

Figure 5E:
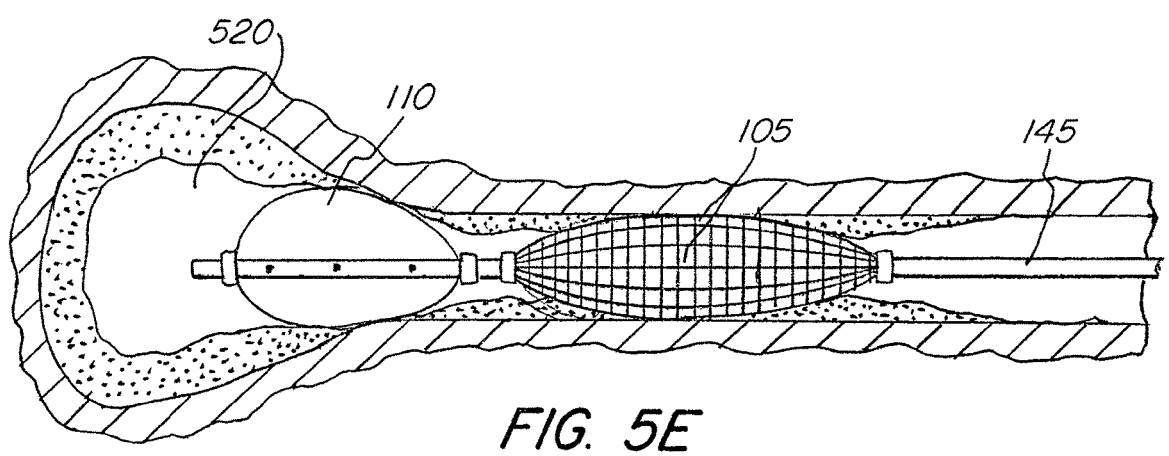
Figure 5F:
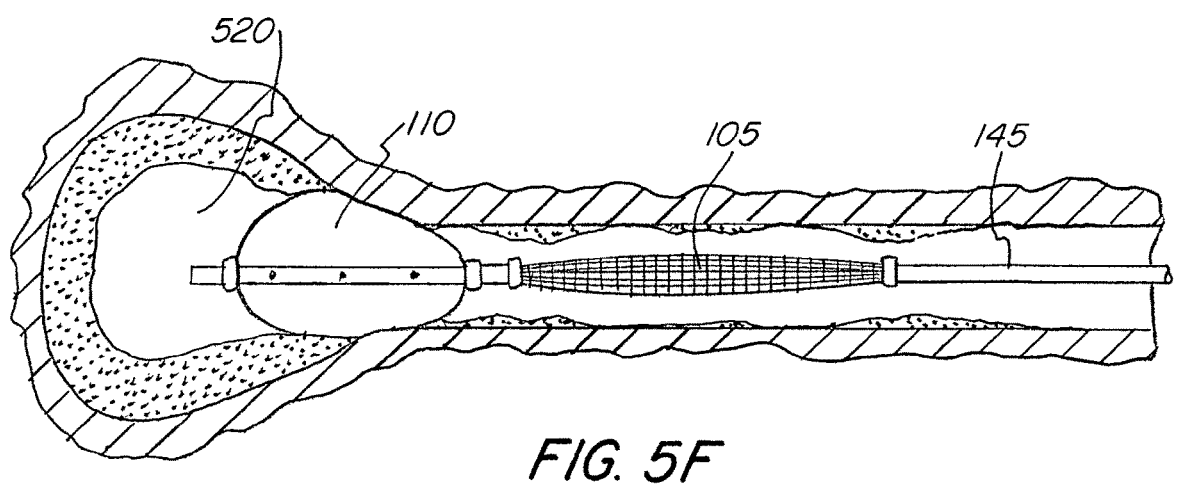

Referring to FIGS. 5E-F, resection balloon (110) is then similarly inflated by pump (120). Balloon (110) is repeatedly inflated and deflated in pulsed fashion such that the mesh gradually and non-traumatically resects the biological material forming the obstruction in the sinus ostia, as further described in more detail below. Because dilation balloon (110) is kept in an inflated state while this resection takes place, the biological material resected from the sinus ostium is prevented from travelling up into the sinus. As the pump (120) is operated, data from the measurements and calculations is continuously updated and displayed.

Figure 5G:
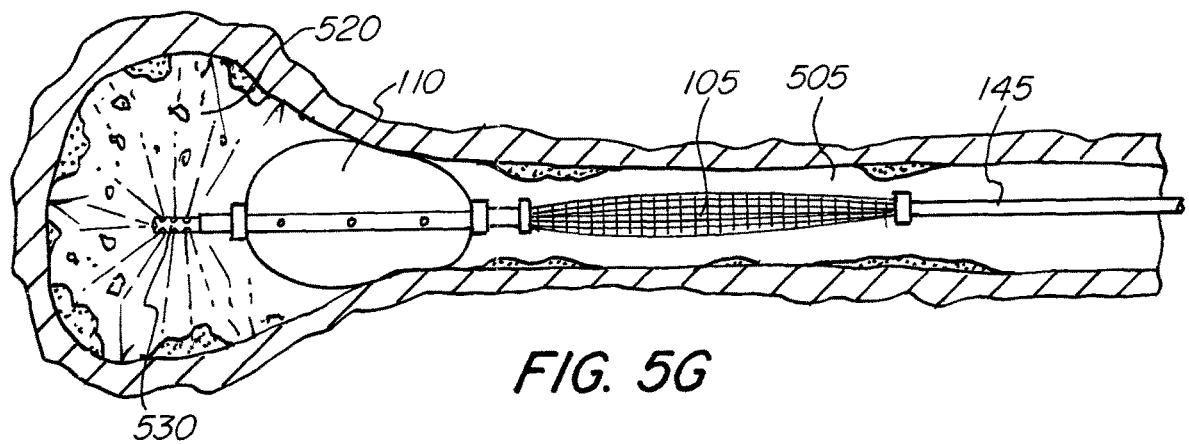

Referring to FIG. 5G, one or more fluids can then be delivered to the sinus (520) via the tip (530) of the catheter (145). In particular, a lumen of the catheter (145) may be used to communicate a fluid, such as saline, from an irrigation fluid source, which may or may not be part of pump (120), to the sinus (520) in order to rinse the area and allow undesirable buildup to drain out through the now-unobstructed sinus ostia (505). The irrigation fluid source may be part of pump (120) or a separate device. The catheter tip (530) may have a plurality a very small openings, such as a plurality of holes in the radial outer wall of the distal end of the catheter, in order to deliver the irrigation fluid to the walls of the sinus (520) at high pressure. Similarly, any of the aforementioned therapeutic and/or diagnostic agents may be delivered from a therapeutic agent source, which may or may not be part of pump (120), to the sinus (520) in similar fashion.

Figure 5H:
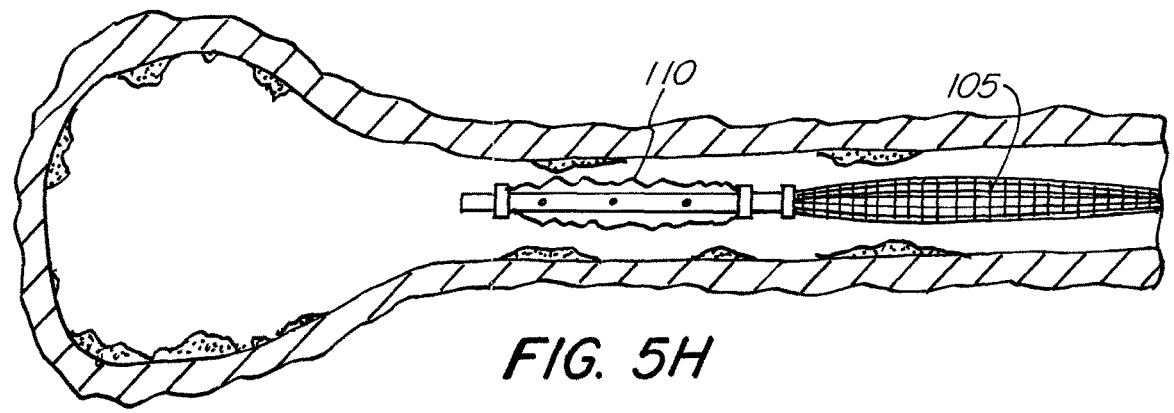
Figure 5I:
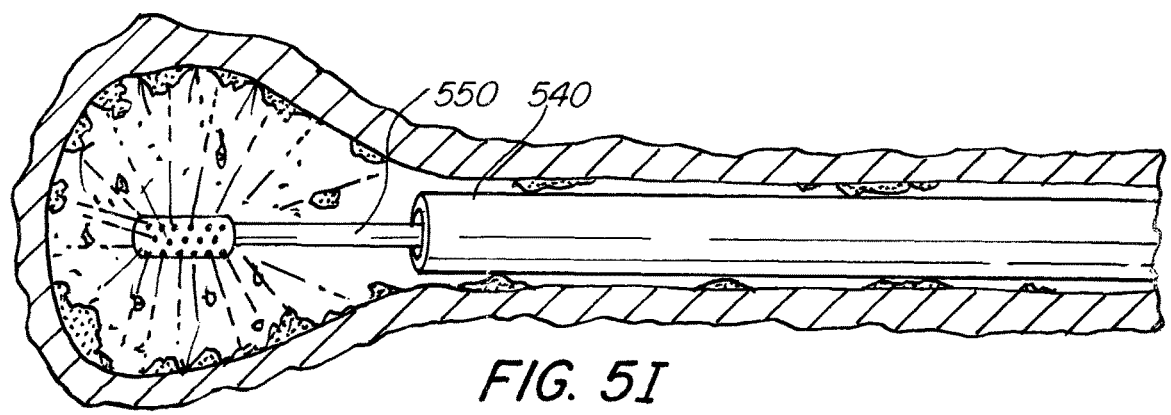

Referring to FIG. 5H, if balloons (105, 110) are not already both deflated, they are now deflated and catheter (145) is withdrawn. As shown in FIG. 5H, a cannula (540) may be inserted into and advanced through the sinus ostium, either before or after the catheter (145) is withdrawn, in order to facilitate draining the sinus (520). A probe (550) may be advanced through the cannula (540) and deliver an irrigation fluid and/or therapeutic agent to the sinus (520) in a manner similar to that described above for catheter (145).

Figure 6A:
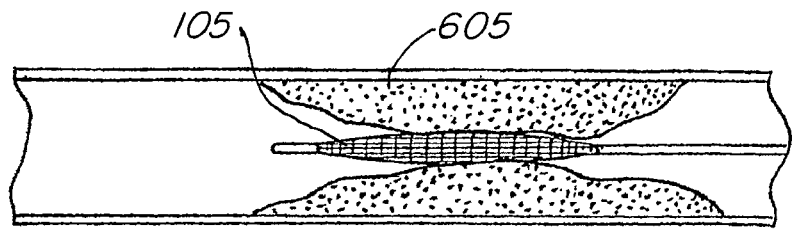
FIGS. 6A-F are exposed, side views of the resection balloon of FIG. 1 being operated in a sinus ostium.
Figure 6B:
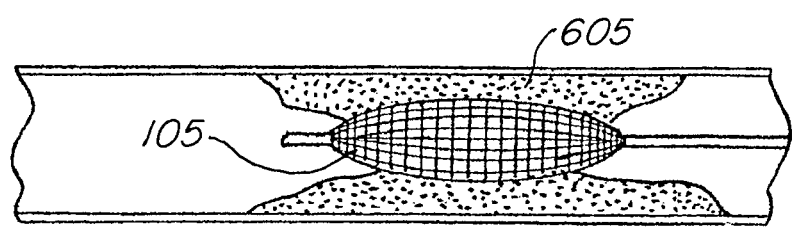

The process of resection is more clearly shown in FIGS. 6A-F, which for purposes of illustration only, depict only resection balloon (105). Referring first to FIGS. 6A-B, resection balloon (105) is inflated by the pump (120), and the pump (120) calculates the initial approximation of the density of the biological material (605) and the size of the opening in which it is located, and displays the results for confirmation by the physician.

Figure 6C:
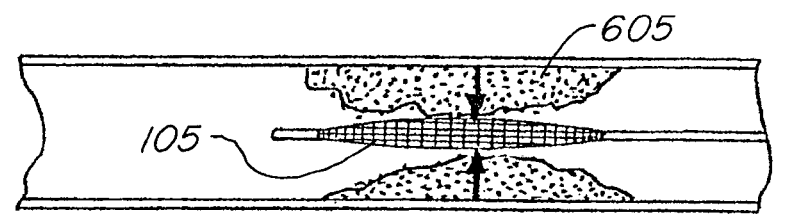
Figure 6D:
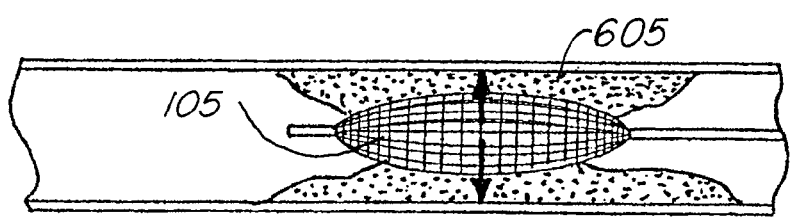

Then, as shown in FIGS. 6C-D, when a pulse button on the pump (120) is pressed, the pump (120) causes resection balloon (105) to pulsate according to a desired frequency or change in volume within the balloon, producing a periodically recurring increase and decrease in balloon size. Accordingly, the resecting surface (205) of resection balloon (105) repeatedly comes into contact with the biological material (605) to create micro-impacts thereon. As the resection balloon (105) is deflated and inflated, the resecting surface (205) creates just enough interference fixation, concentrically, along with compressive force excitation and friction upon the unwanted biological material (605), to promote compressive force exhaustion and abrasion to elicit the decomposition and excision thereof, such that the targeted biological material (605) is resected in a non-traumatic way.

Additionally, the fluid used to inflate resection balloon (105) can be heated or cooled, thereby heating or cooling resection balloon (105) to aid in the resection of the biological material. As the biological material (605) is destroyed and removed, resection balloon (105) is inflated to a larger starting diameter and these steps are repeated until all the unwanted biological material (605) is resected.

Meanwhile, the pump continually monitors the balloon pressure and gas flow of resection balloon (105), and it updates a graphical display (130) accordingly. This gives the physician an indication as to when to stop the pulse mode and evacuate the loosened biological material (605).

Figure 6E:
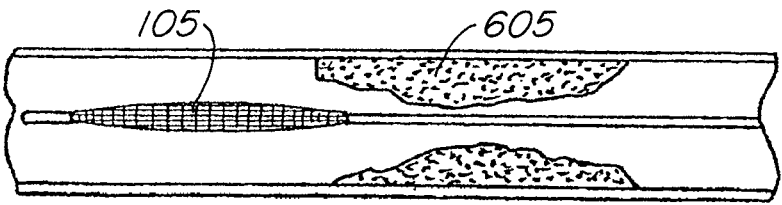

Referring to FIG. 6E, once the obstruction is broken up, resection balloon (105) and dilation balloon (110) are deflated (by pressing a deflate button on the pump), and resection balloon (105) is inserted further distally into the bodily cavity, past the location of unwanted biological material (605).

Figure 6F:
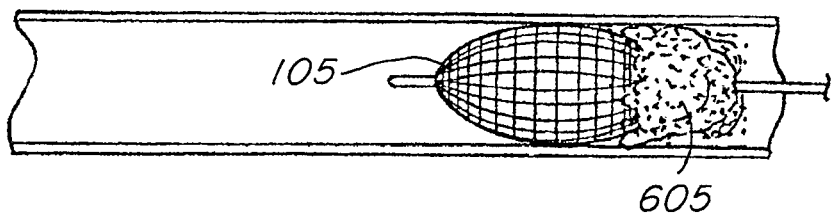

A shown in FIG. 6F, resection balloon (105) is then re-inflated (by pressing the inflate button on the pump) and gently pulled towards the proximal end, bringing with it the loose biological material (605) and debris to a point where it can be removed using forceps or suction. The debris may also be removed through one of the available lumens.

Figure 7A:
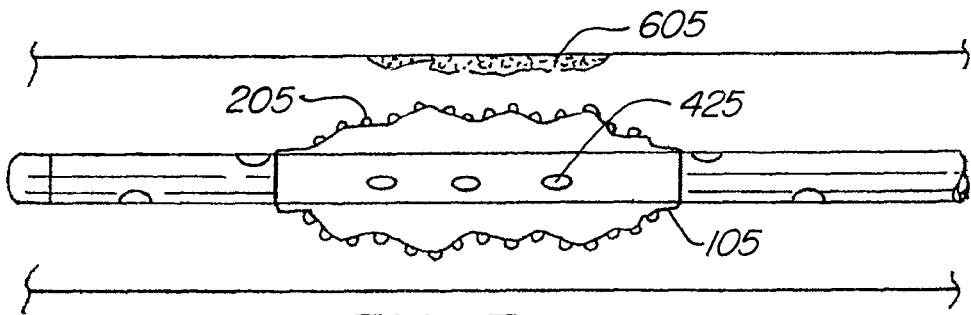
FIGS. 7A-D are exposed, side views of the catheter of FIG. 1 being used to facilitate drug delivery in a sinus ostium.
Figure 7B:
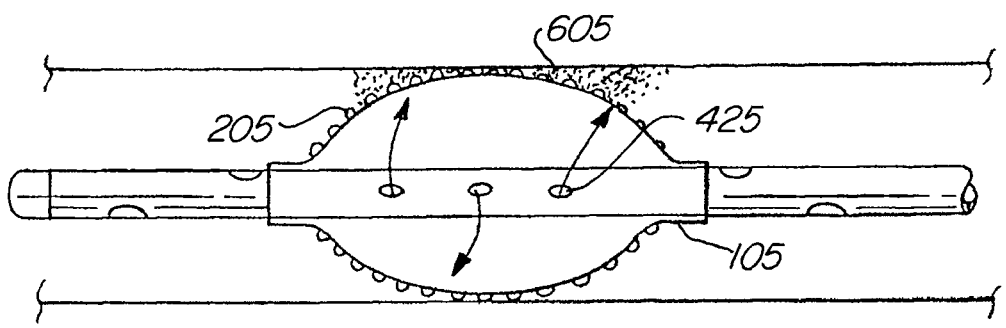

A method for operation of the catheter system (100) for delivering a therapeutic and/or diagnostic agent to biological material in the nose, nasal cavity, or paranasal sinuses is generally described with reference to FIGS. 7A-D, which for purposes of illustration only, depict only resection balloon (105). As shown in FIGS. 7A-B, after the dilation balloon is inflated, resection balloon (105) is inflated by the pump (120). This causes the abrasive outer surface (205) of balloon (105) to contact the biological material (605) and creates surface abrasions in the biological material. The surface abrasions act to create capillary blood flow and to instigate flow of white blood cells to the biological material, which facilitates absorption of an agent into the biological material. A pressure regulator and flow meter along with the known dimensions of the balloon provide feedback to the pump (120) necessary to determine dimensions and resistance of the biological material from which a determination is made as to the diameter of the ostium and the density of the biological material (605). Using theses parameters, a microcontroller makes the appropriate pressure and timing adjustments necessary to maximize the effectiveness of the balloon, provide the physiologic metrics of the affected and non-affected areas, and provide data points and indicators related to the specific dimensional and density characteristics of the intra-ostial anatomy and pathology and aid the physician in safely determining and delivering treatment.

Resection balloon (105) can be sequentially pulsed to create further surface abrasions. When a pulse button on pump (120) is pressed, resection balloon (105) is deflated and inflated in a cyclical fashion, based either on parameters that were entered by the user, or on default parameters selected by the pump (120), which are based on the characteristics of the particular balloon (which has been identified as a result of the aforementioned balloon identification plate) and the diameter and/or density measurements made by the system. In this way, the pulse mode of the pump (120) causes resection balloon (105) to pulsate according to a desired frequency or change in volume within the balloon, producing a periodically recurring increase and decrease in balloon size.

Figure 7C:
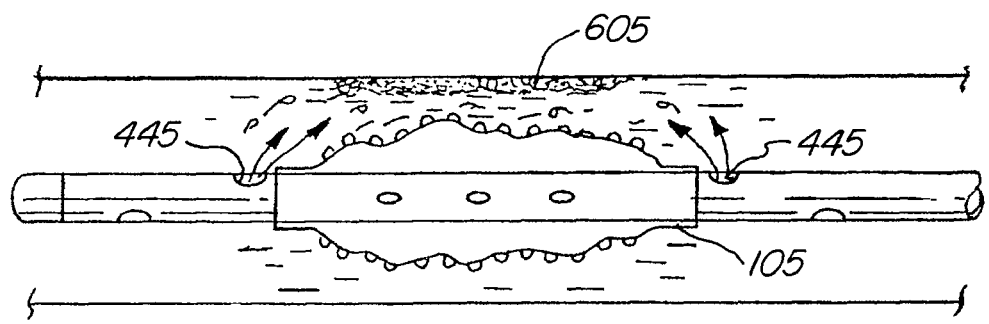

As shown in FIG. 7C, a therapeutic and/or diagnostic agent is then delivered via the openings (445) passing through the wall of the catheter (145). It should be noted, however, that the agent can also be delivered through a plurality of openings provided in the wall of the resection balloon (105).

As the agent is delivered, it coats the outer surface of resection balloon (105). Resection balloon (105) is inflated, such that the outer surface of first balloon (105) contacts the biological material (605), and is kept that way for a desired period of time. Resection balloon (105) is then at least partially deflated, recoated with the agent, re-inflated and kept that way again. This sequential and/or constant expansion of resection balloon (105) instigates extravasation and initiates fluid extravasation through the vessel walls and into the adjacent biological material.

Figure 7D:
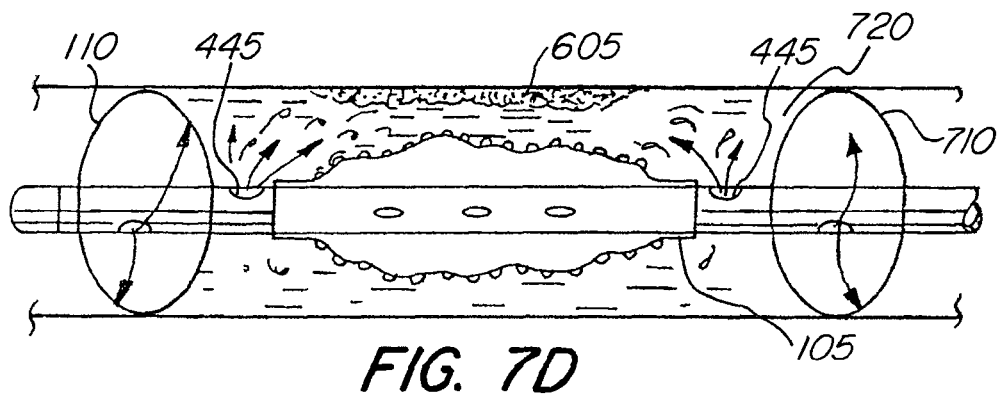

As shown in FIG. 7D, in certain advantageous embodiments, the catheter (145) includes an additional balloon (710). As a result, balloons (110, 710), if both inflated, can create a chamber (720) into which the therapeutic agent is delivered. Further, the fluid pressure can be increased by inflating balloon (105) inside this chamber, further helping to extravasate the therapeutic agent into the surrounding tissue.

Once the agents have been delivered and extravasted into the biological material (605) at the target site, any remaining agent can be evacuated via the same openings (445) and lumens through which they were supplied using suction. Pump (120) may provide a negative pressure to vacuum out the agents. The various lumens and corresponding openings (445) can be used to cyclically deliver and evacuate the agents and various other fluids instantly, sequentially, intermittently and/or continuously over designated time intervals.

It should be noted that, while various balloon abrading and extravastion methods for aiding drug delivery have been described above, such methods are not required, and therapeutic agents can simply be delivered to the target site via the opening (445). Further, while the resecting and abrading have been described with respect to the pulsation mechanism of action described herein, such action is not exclusive, and other mechanisms of action may be employed in addition to pulsation as needed, such as linear translation of the balloon along the catheter, as well as rotation. These motions are particularly useful in mucosa resection.

Figure 8:
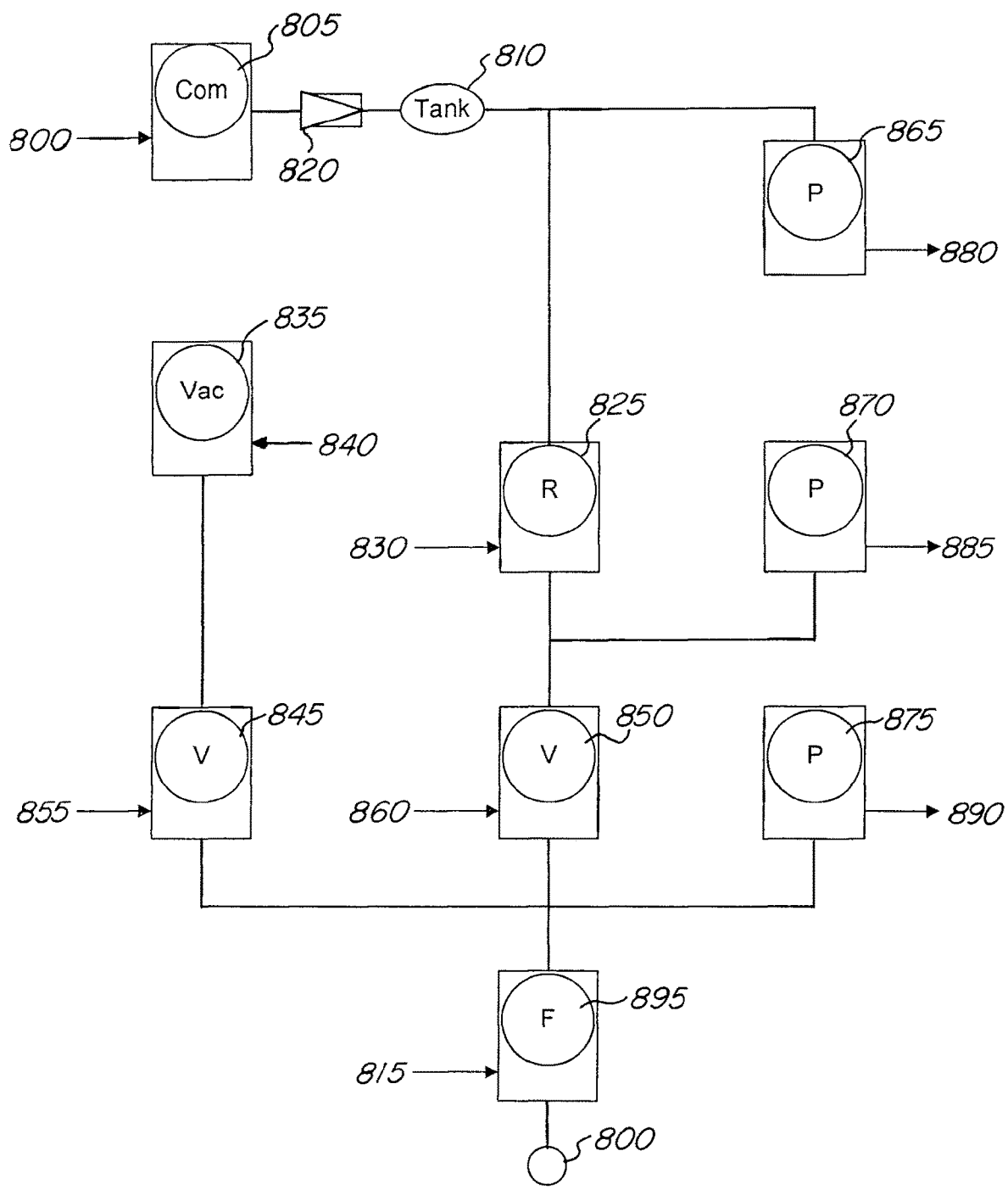
FIG. 8 is a block diagram illustrating the pneumatics of the pump of FIG. 1.

A pump (120) that controls the operation of balloons (105, 110) described above will hereafter be described. FIG. 8 represents a block diagram of the pneumatic components and operation of the pump. The pump includes an air compressor (805) and a pressure tank (810), such as a Festo model CRVZS-0.1, which enable it to achieve up to 10 atmospheres of continuous pressure. The air pressure in the tank (810) is continuously monitored by a microcontroller (815). The microcontroller initiates the compressor (805) to operate via an electrical signal output (800) when the tank pressure drops below 4-5 atmospheres. The size of the tank (810) is selected such that at least one procedure can be completed without the compressor operating. The microcontroller calculates and displays the amount of air in the tank (810), which indicates to the user whether there is enough air to complete the procedure. A check valve (820), such as a Festo model H-1/8-A/1, is located between the compressor (805) and the tank (810) in order to prevent the pressured gas from flowing back into the compressor (805). In another variation of the pump (120), however, the above-referenced compressor and pressure tank are not included, and the pressurized air or carbon dioxide is instead provided from an external source, such as a hand actuated pump, $CO_2$ cartridge, gas tank or the operating room walls commonly found in an operating room.

The pressurized gas from the air tank (810) first goes through a pressure regulator (825), which is electronically controlled via an analog electrical output (0V-10V) signal (830) generated by the microcontroller to supply air to a balloon at an exact pressure, which can be set and changed by the physician. However, any pressures higher than the upper limit for the particular balloon being used will generate a warning signal. As explained above, different balloon catheters may be used depending on the application, which are identifiable via key connectors. Therefore, pressure, volume, and flow characteristics of different types of balloons are contained in lookup tables in order to optimize the operation of the balloons and to ensure their consistent performance.

Accordingly, when the pressure is set higher than the balloon's upper limit, the detection of gas flow will cause the pump to stop and produce a warning, and the physician must then take a specific action to override this condition. Similarly, if there is no balloon pressure, the detection of gas flow will also generate a warning, as this may mean the balloon has ruptured. It should further be noted that the pump will also not operate if a catheter is not connected. Additionally, a balloon's operation when first removed from the packaging may vary from its normal operation, requiring that they are first exercised before use in the body. Therefore, the setup and preparation function of the pump allows for this variance.

In certain advantageous embodiments, a vacuum source (835), such as a Festo model VN-05-L-T3-PQ2-VQ2-R01-B, is also included in the pump so that the balloon can be rapidly deflated in a consistent manner. This component also aids in achieving higher frequencies during the pulse mode of operation. The vacuum source (835) is turned on and off by the microcontroller via an electrical output signal (840).

Two microprocessor-controlled solenoid valves—a deflation valve (845) and an inflation valve (850)—are used to control the inflation and deflation of the balloon. The appropriate balloon inflation size is achieved by keeping the gas pressure constant, using the balloon pressure, flow, and volume characteristics from the lookup table data, and timing the on/off activation periods of the valves (845, 850). Deflation valve (845) and inflation valve (850) are controlled by a deflate electrical signal (855) and an inflate electrical signal (860), respectively, which are generated by the aforementioned microcontroller.

The gas pressure is continuously monitored by the microcontroller using pressure regulator (865) at the input from the tank (810), a pressure regulator (870) at the output of the regulator (825), and pressure regulator (875) at the output to the balloon. These pressure regulators, which may be, for example, Festo model SDET-22T-D10-G14-U-M12, provide to the microcontroller analog electrical signal (0V-10V) inputs (880, 885, 890) that vary proportionally to the pressure at the regulators (865, 870, 875). The gas passes through an electronic flow meter (895), such as a Festo model SFET-F010-L-WQ6-B-K1, and a filter (899), before being delivered to the balloon. The flow meter (895) provides an analog electrical signal input (815) to the microcontroller that indicates the amount of gas flow to the balloon.

The pressure regulator (875) and flow meter (895), along with the known dimensions of the balloon, provide the feedback necessary to determine the ostial wall or biological material dimensions and resistance via circumferential force and depth resistance, from which a determination is made as to the ostial diameter or the density of the biological material. Using these parameters, the microcontroller makes the appropriate pressure and timing adjustments necessary to maximize the effectiveness of the balloon, provide the physiologic metrics of the affected and non-affected areas, and provide data points and indicators related to the specific dimensional and density characteristics of the intra-lumen anatomy and pathology to aid the physician in safely determining and delivering treatment.

Using the method above, the gas pressure is strictly monitored and maintained at 2 atmospheres in order to keep the balloon from bursting. The high gas input pressure (up to 10 atmospheres) is reduced to and regulated at 2 atmospheres electronically and under software control. However, the pressure delivered to the balloon can be increased or decreased under certain conditions via operator commands.

A further explanation of the components and operation of the pump (120) is provided in U.S. Pat. No. 8,226,601 to Gunday et al., the specification of which is hereby incorporated by reference herein in its entirety.

Alternatively, one can use a handheld apparatus to inflate and deflate the balloons. For example, one could use a ball pump that remains outside of the body and is connected to the balloon, which includes a pressure gauge. The measurements can be collected by sequential inflation of the balloon using the pump. Alternatively, the device could include transducers at the distal end of the catheter or on the balloon, and it may display its measurements as a digital readout. In other cases, an instrument such as a tenaculum could be used to slowly open and control/measure the ostium. The hand actuator can employ a $CO_2$ cartridge in the actuator and be used in conjunction with a mobile device application (e.g., iPhone app), to measure pressure and volume.

Although the above described methods are described with reference to the sinus ostia, the methods of the present invention are suitable for transnasal dilation of other passageways in the ear, nose and/or throat, such as the Eustachian tube and nasolacrimal duct.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for clearing a sinus ostium of a patient, the method comprising:
    inserting a catheter assembly into the sinus ostium, the catheter assembly having a resection balloon with a resecting surface and a dilation balloon;
    positioning the resection balloon at an obstruction in the sinus ostium, and the dilation balloon distal to the resection balloon;
    dilating a portion of the sinus ostium by inflating the dilation balloon while the dilation balloon is distal to the resection balloon;
    resecting material from the obstruction by repeatedly inflating and deflating the resection balloon while the dilation balloon is distal to the resection balloon such that the resecting surface resects the material.

2. The method of claim 1, further comprising the steps of: deflating the dilation balloon; and
    clearing resected material from the sinus ostium by removing the catheter assembly from the sinus ostium while the resection balloon is inflated.

3. The method of claim 1, wherein the resecting surface comprises a mesh on an outer surface of the resection balloon.

4. The method of claim 3, wherein the mesh comprises elastane.

5. The method of claim 3, further comprising the step of delivering thermal energy to the mesh to aid the resection of the material.

6. The method of claim 3, wherein the mesh is impregnated with a therapeutic agent.

7. The method of claim 1, wherein the step of inflating the resection balloon comprises delivering a fluid that heats the resection balloon to aid the resection of the material.

8. The method of claim 1, wherein the step of inflating the resection balloon comprises delivering a fluid that cools the resection balloon to aid the resection of the material.

9. The method of claim 1, further comprising the step of flushing the sinus by delivering a fluid thereto.

10. The method of claim 9, wherein the fluid delivered to the sinus is saline.

11. The method of claim 9, wherein the catheter assembly comprises a catheter having a radial outer wall, and the step of flushing the sinus comprises urging the fluid through a plurality of holes passing through the radial outer wall of the catheter.

12. The method of claim 1, further comprising the step of advancing a cannula over the catheter assembly into the sinus ostium and removing the catheter assembly from the sinus ostium to drain the sinus.

13. The method of claim 1, further comprising the step of delivering a therapeutic agent to the sinus.

14. The method of claim 1, further comprising the step of delivering a therapeutic agent to the obstruction.

15. The method of claim 1, further comprising the step of viewing the sinus ostium and/or sinus by advancing an imaging device through the catheter assembly.

* * * * *